(12) United States Patent
Fujita

(10) Patent No.: US 9,435,639 B2
(45) Date of Patent: Sep. 6, 2016

(54) OPTICAL SENSOR

(71) Applicant: OLYMPUS CORPORATION, Tokyo (JP)

(72) Inventor: Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 218 days.

(21) Appl. No.: 14/453,035

(22) Filed: Aug. 6, 2014

(65) Prior Publication Data

US 2014/0346331 A1 Nov. 27, 2014

Related U.S. Application Data

(63) Continuation of application No. PCT/JP2013/050839, filed on Jan. 17, 2013.

(30) Foreign Application Priority Data

Feb. 10, 2012 (JP) .................. 2012-027192

(51) Int. Cl.
*G01B 11/24* (2006.01)
*G01B 11/16* (2006.01)
(Continued)

(52) U.S. Cl.
CPC .............. *G01B 11/24* (2013.01); *G01B 11/18* (2013.01); *G01D 5/268* (2013.01); *G01D 5/285* (2013.01); *G01D 5/35374* (2013.01);
(Continued)

(58) Field of Classification Search
CPC ................ G01B 11/24; G01J 1/0425; G02B 2006/12111; G01D 5/35374

USPC ................................................... 250/227.14
See application file for complete search history.

(56) References Cited

U.S. PATENT DOCUMENTS

| 4,899,046 A | 2/1990 | Wright et al. |
| 8,119,069 B2 * | 2/2012 | Petrich ............... G01N 21/8483 |
| | | 422/82.05 |

(Continued)

FOREIGN PATENT DOCUMENTS

| CN | 1484750 A | 3/2004 |
| CN | 1695041 A | 11/2005 |

(Continued)

OTHER PUBLICATIONS

Japanese Office Action dated Mar. 8, 2016 from related Japanese Patent Application No. 2012-027192, together with an English language translation.

(Continued)

*Primary Examiner* — Seung C Sohn
(74) *Attorney, Agent, or Firm* — Scully, Scott, Murphy & Presser, PC

(57) ABSTRACT

An optical sensor includes a light source, a characteristic light-guiding member, a characteristic changing part which changes the optical characteristic of light, and a detecting unit which detects the light having the optical characteristic changed by the characteristic changing part and guided by the characteristic light-guiding member. The optical sensor includes a control member which inhibits at least the twisting of the characteristic light-guiding member, and controls a bending state of the characteristic light-guiding member, and a positioning mechanism which positions the characteristic changing part with respect to at least a circumferential direction of the characteristic light-guiding member.

7 Claims, 11 Drawing Sheets

(51) Int. Cl.
  *G01D 5/353* (2006.01)
  *G01D 5/26* (2006.01)
  *G01J 1/04* (2006.01)
  *G01D 5/28* (2006.01)
  *G02B 6/36* (2006.01)
  *G02B 6/12* (2006.01)

(52) U.S. Cl.
  CPC .......... *G01J 1/0425* (2013.01); *G02B 6/3616* (2013.01); *G02B 2006/12111* (2013.01); *G02B 2006/12138* (2013.01)

(56) References Cited

U.S. PATENT DOCUMENTS

| | | | |
|---|---|---|---|
| 9,228,825 B2 * | 1/2016 | Takaura | ............... G01B 11/043 |
| 2002/0088931 A1 | 7/2002 | Danisch et al. | |
| 2002/0183592 A1 | 12/2002 | Suzuki et al. | |
| 2006/0001863 A1 | 1/2006 | Kishida et al. | |
| 2007/0116415 A1 | 5/2007 | Kobayashi | |

FOREIGN PATENT DOCUMENTS

| | | |
|---|---|---|
| JP | 57-141604 A | 9/1982 |
| JP | 2001-318011 A | 11/2001 |
| JP | 2002-345730 A | 12/2002 |
| JP | 2004-094032 A | 3/2004 |
| JP | 2004-134288 A | 4/2004 |
| JP | 2007-143600 A | 6/2007 |
| JP | 2007-248213 A | 9/2007 |

OTHER PUBLICATIONS

Chinese Office Action dated Jan. 22, 2016 from related Chinese Patent Application No. 201380008646.8, together with an English language translation.

International Search Report dated Feb. 19, 2013 issued in PCT/JP2013/050839.

Japanese Office Action dated Aug. 18, 2015 from related Japanese Patent Application No. 2012-027192 , together with an English language translation.

International Preliminary Report on Patentability together with the Written Opinion of the International Searching Authority from related International Application No. PCT/JP2013/050839, dated Aug. 21, 2014.

Extended Supplementary European Search Report dated Oct. 23, 2015 from related European Application No. 13 74 7315.3.

* cited by examiner

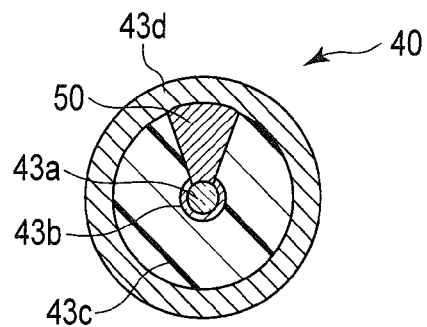
F I G. 1B
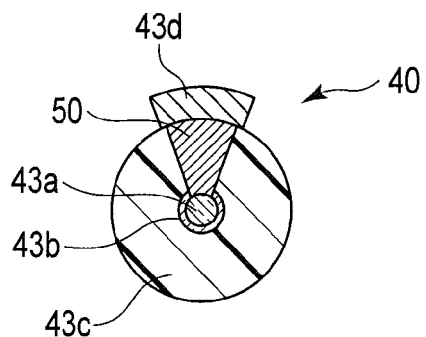
F I G. 1C
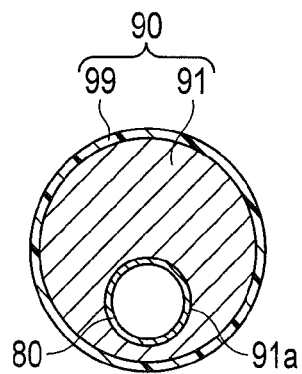
F I G. 1D

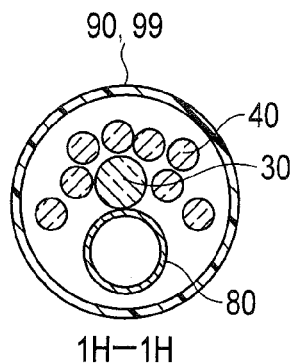
F I G. 1H
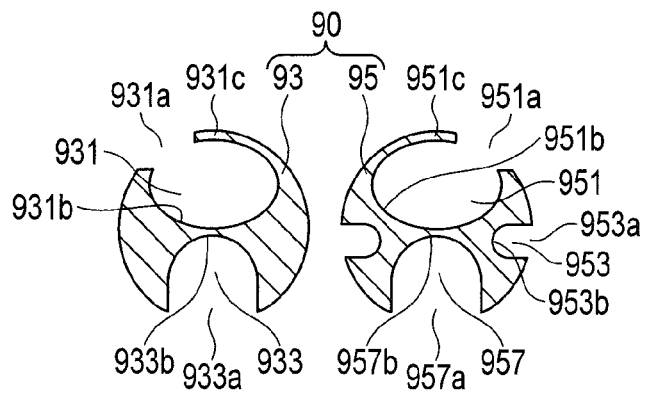
F I G. 2
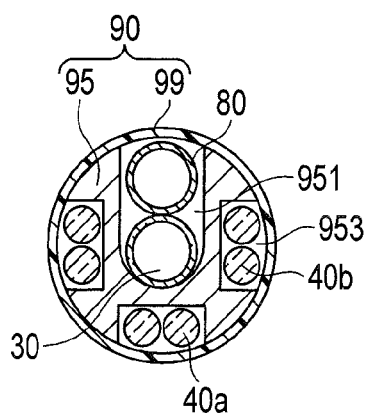
F I G. 3

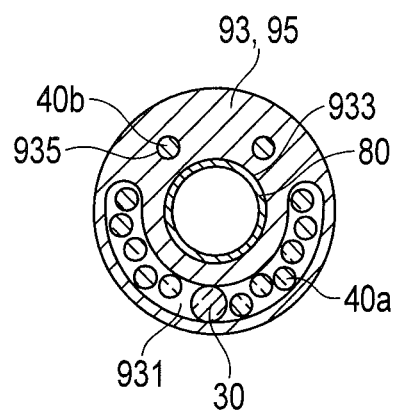
F I G. 4A
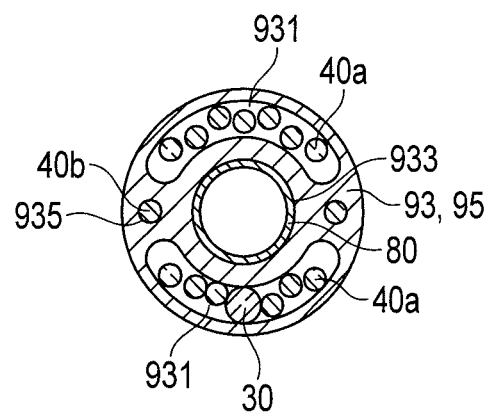
F I G. 4B

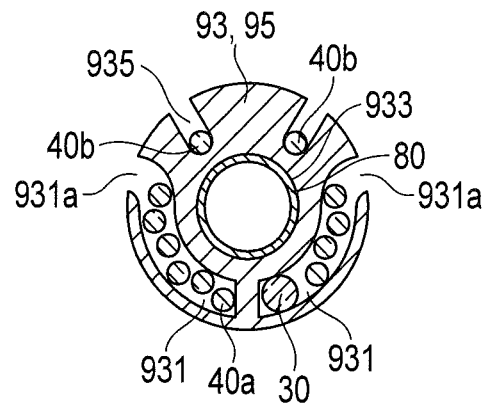
F I G. 4C
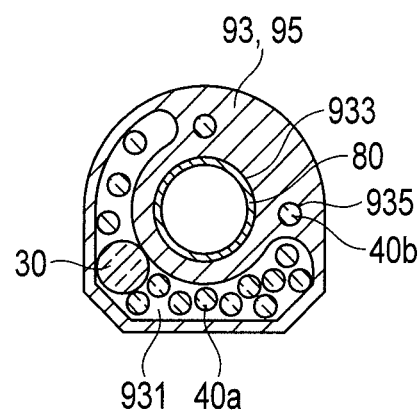
F I G. 4D

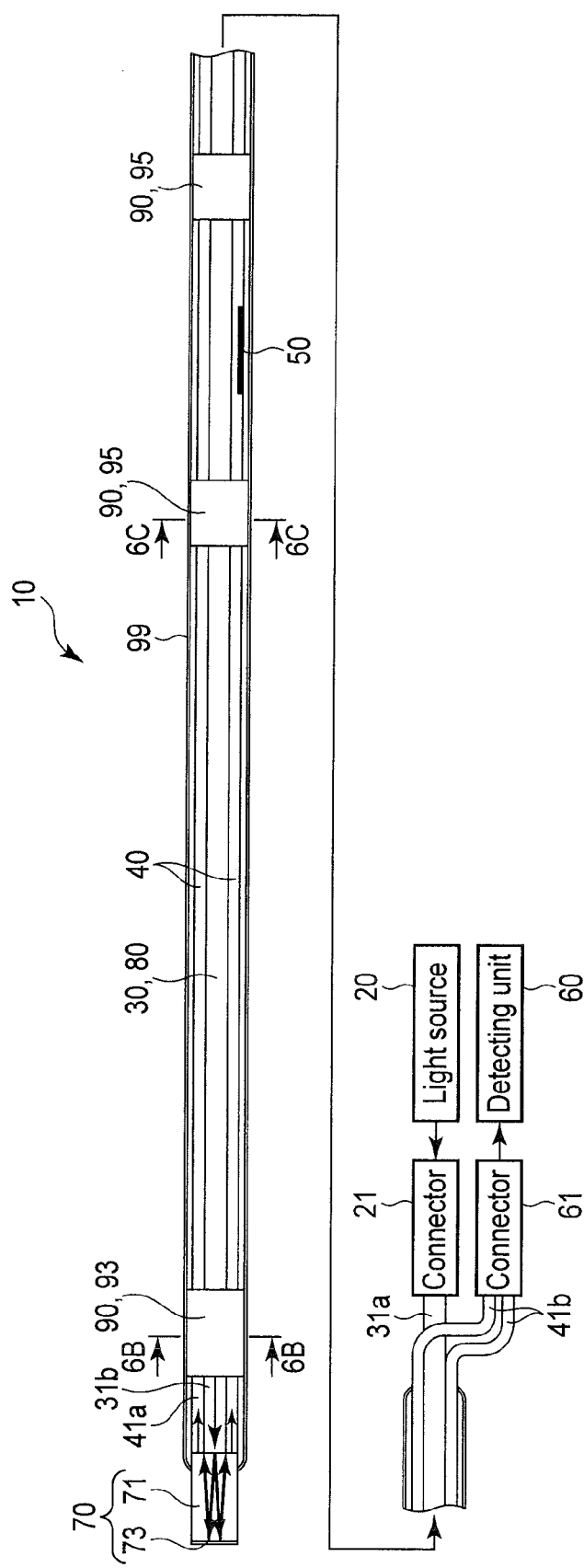
F I G. 6A

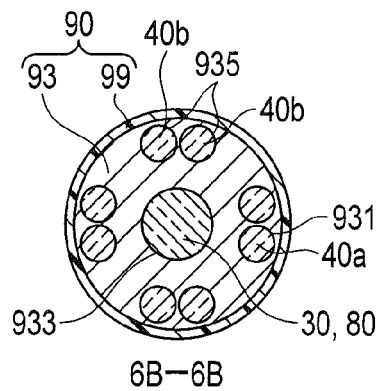
F I G. 6B
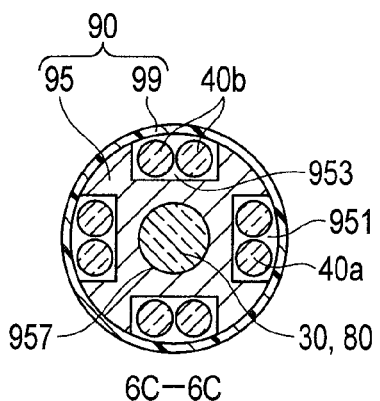
F I G. 6C
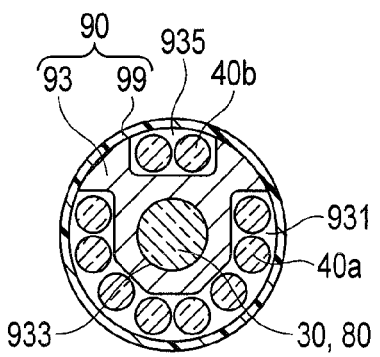
F I G. 6D

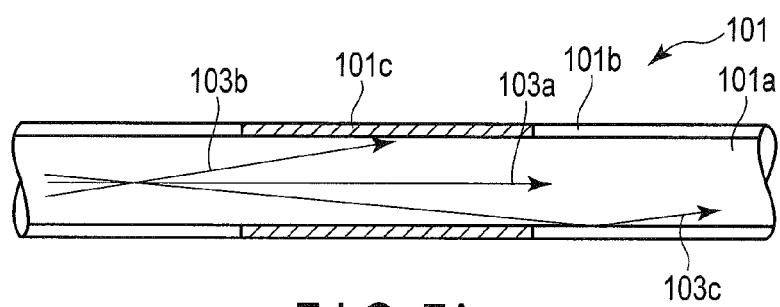
F I G. 7A
General Art
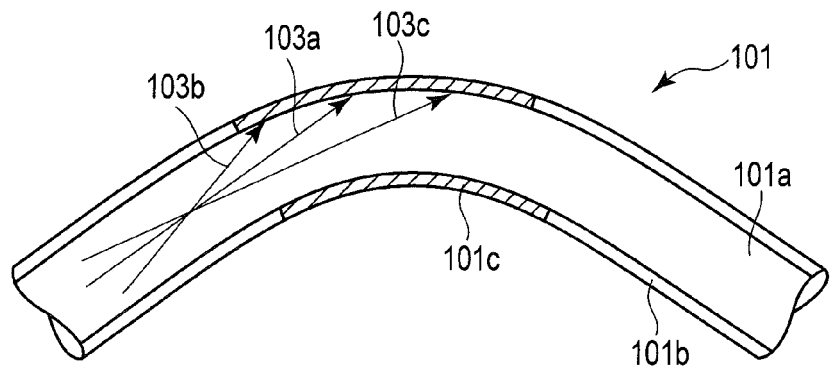
F I G. 7B
General Art
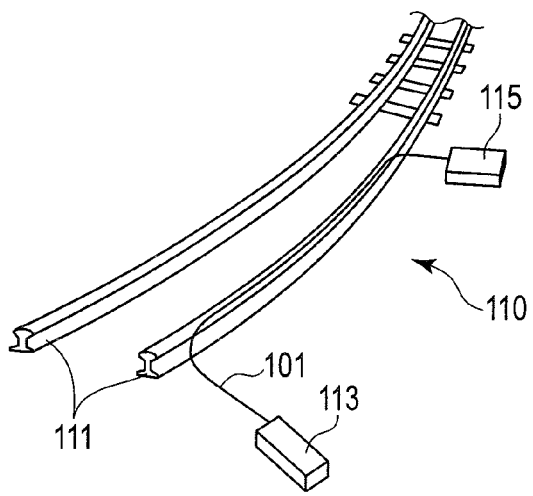
F I G. 7C
General Art

OPTICAL SENSOR

CROSS-REFERENCE TO RELATED APPLICATIONS

This application is a Continuation application of PCT Application No. PCT/JP2013/050839, filed Jan. 17, 2013 and based upon and claiming the benefit of priority from prior Japanese Patent Application No. 2012-027192, filed Feb. 10, 2012, the entire contents of all of which are incorporated herein by reference.

BACKGROUND OF THE INVENTION

1. Field of the Invention

The present invention relates to an optical sensor.

2. Description of the Related Art

Jpn. Pat. Appln. KOKAI Publication 57-141604, for example, discloses an optical fiber. As shown in FIG. 7A, the optical fiber 101 has a core 101a, a cladding 101b covering the core 101a, and a light absorbing part 101c which is provided in the cladding 101b.

How light propagates in the optical fiber 101 will be explained.

In this case, the optical fiber 101 may extend straight as shown in FIG. 7A, all of light 103a is guided in the axial direction of the optical fiber 101. The light 103b propagating at a first angle to the axial direction is absorbed in the light absorbing part 101c. The light 103c propagating at a second angle to the axial direction is not absorbed in the light absorbing part 101c, and is completely reflected by the cladding 101b and is guided forwards.

As shown in FIG. 7B, when the optical fiber 101 may be bent at the light absorbing part 101c, light beams 103, 103b, and 103c propagate toward the light absorbing part 101c. As a result, the light beams 103, 103b, and 103c are absorbed in the light absorbing part 101c, and will no longer propagate.

The light intensity guided is thus controlled.

Such the optical fiber 101 is used a curvature measuring device 110 as shown in FIG. 7C which detects the dislocation of the optical fiber 101 and which is a representative optical sensor. The curvature measuring device 110 shown in FIG. 7C has an optical fiber 101 shown in FIG. 7A and laid along a rail 111, a laser light source 113 connected to one end of the optical fiber 101, and a photoelectric transducer device 115 connected to the other end of the optical fiber 101. The optical fiber 101 is bent to match the curvature of the rail 111. In proportion to the curvature of the rail 111, the light decreases in intensity as it propagates in the optical fiber 101 from the laser light source 113 to the photoelectric transducer device 115. The photoelectric transducer device 115 measures the decrease in the light intensity in compliance with the curvature. Therefor the curvature of the rail 111 and the downward flexure of the rail 111 can be measured.

The light absorbing part 101c, i.e., characteristic changing part, is positioned as shown in FIG. 7A. In the optical sensor shown in FIG. 7C, the optical fiber 101 is provided such that the light absorbing part 101c is located for example, on the outer circumference face side of the bending rail 111. Thus, the optical fiber 101 including the light absorbing part 101c is provided in accordance with the direction in which the rail 111 is bent.

However, if the optical fiber 101 is provided in, for example, a small high-precision device that is long, thin and flexible, it will be twisted as the high-precision device is twisted and bent, the optical fiber 101 is twisted. Consequently, the characteristic changing part is dislocated, rendering it difficult to detect the state of the high-precision device.

This invention has been made in view of the above. An object of the invention is to provide an optical sensor in which the characteristic changing part can be reliably positioned and the statuses of the components can be detected accurately and easily.

BRIEF SUMMARY OF THE INVENTION

An aspect of an optical sensor according to this invention includes a light source configured to emit light; a characteristic light-guiding member configured to guide the light emitted from the light source; a characteristic changing part which is provided in the characteristic light-guiding member and configured to change the optical characteristic of the light in accordance with how much the characteristic light-guiding member is bent; a detecting unit configured to detect the light having the optical characteristic changed by the characteristic changing part and guided by the characteristic light-guiding member; a control member which provided along the characteristic light-guiding member, configured to inhibit at least the twisting of the characteristic light-guiding member, and controls a bending state of the characteristic light-guiding member; and a positioning mechanism which holds the characteristic light-guiding member and the control member and positions the characteristic changing part with respect to at least a circumferential direction of the characteristic light-guiding member accompanying holding.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1B is a sectional view of a characteristic light-guiding member including a characteristic changing part;

FIG. 1C is a sectional view of the characteristic light-guiding member including a characteristic changing part;

FIG. 1D is a sectional view taken along line 1D-1D shown in FIG. 1A;

FIG. 1H is a sectional view taken along line 1H-1H shown in FIG. 1A;

FIG. 2 is a diagram showing a first modification of a first embodiment;

FIG. 3 is a diagram showing a second modification of the first embodiment;

FIG. 4A is a diagram showing a third modification of the first embodiment;

FIG. 4B is a diagram showing the third modification of the first embodiment;

FIG. 4C is a diagram showing the third modification of the first embodiment;

FIG. 4D is a diagram showing the third modification of the first embodiment;

FIG. 6A is a schematic view of an optical system according to the third embodiment;

FIG. 6B is a sectional view taken along line 6B-6B shown in FIG. 6A;

FIG. 6C is a sectional view taken along line 6C-6C shown in FIG. 6A;

FIG. 6D is a sectional view of a modification taken along line 6B-6B shown in FIG. 6A;

FIG. 7A is a diagram showing an general optical fiber, which extends straight;

FIG. 7B is a diagram showing the optical fiber shown in FIG. 7A in a bent condition; and FIG. 7C is a diagram showing a curvature measuring device which is an optical sensor having an optical fiber of the type shown in FIG. 7A.

DETAILED DESCRIPTION OF THE INVENTION

Embodiments of this invention will be described in detail, with reference to the accompanying drawings. In some figures, to simplify the drawings, some components are not shown, for example, in FIG. 1A, the cover member 97 is not illustrated.

First Embodiment

[Configuration]

A first embodiment is described, with reference to FIG. 1A, FIG. 1B, FIG. 1C, FIG. 1D, FIG. 1E, FIG. 1G, and FIG. 1H.

Figure 1A:
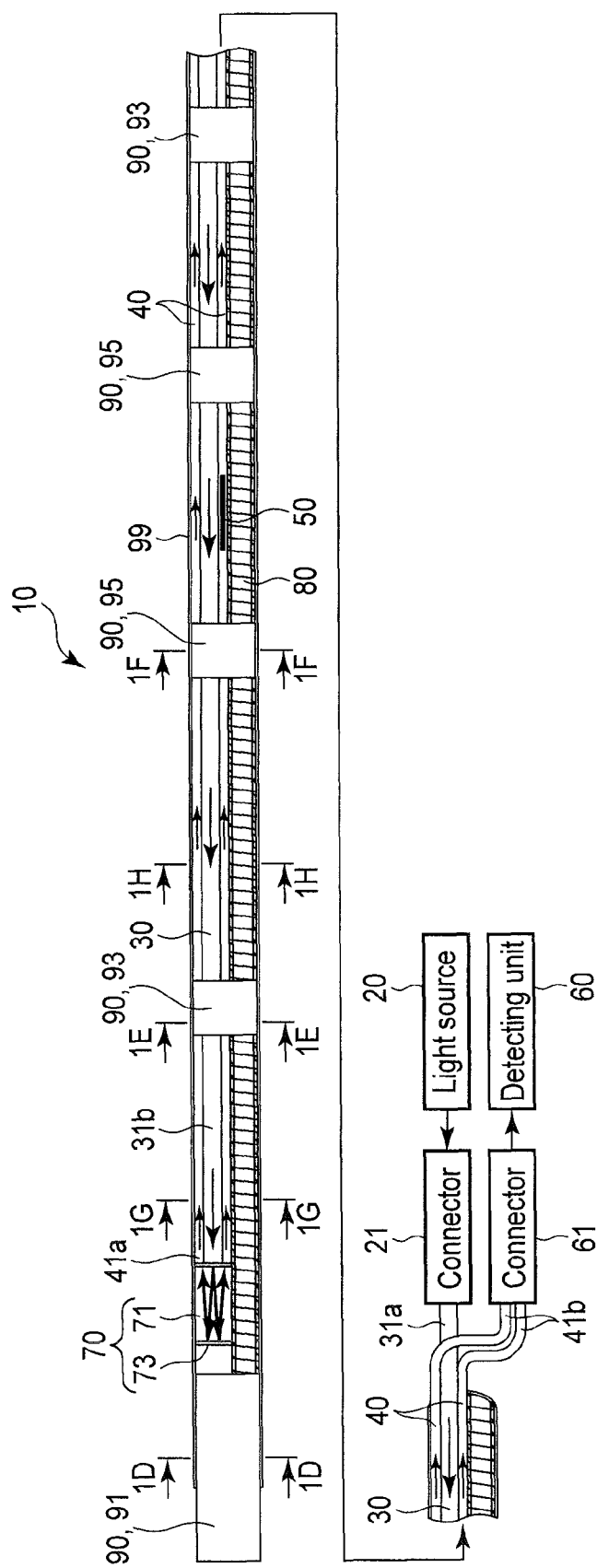
FIG. 1A is a schematic diagram showing an optical system according to a first embodiment of this invention.

As shown in FIG. 1A, an optical sensor 10 has a light source 20 for emitting light, a light supplying/guiding member 30 for guiding the light emitted from the light source 20 to supply the light, and a characteristic light-guiding member 40 for further guiding the light guided by the light supplying/guiding member 30. In addition, the optical sensor 10 has a characteristic changing part 50 which is provided in the characteristic light-guiding member 40 and configured to change the optical characteristic of the light guided by the light-guiding member 40, in accordance with how much the characteristic light-guiding member 40 is bent and a detecting unit 60 which detects the light having the optical characteristic changed by the characteristic changing part 50 and guided by the characteristic light-guiding member 40.

The optical sensor 10 shown in FIG. 1A is provided in a small high-precision device (not shown). The high-precision device is, for example, a thin and long member such as an insertion section of a medical endoscope, an insertion section of an industrial endoscope, a manipulator, or a catheter.

As shown in FIG. 1A, the light source 20 is optically connected by a connector 21 to the light supplying/guiding member 30. The light emitted from the light source 20 is incident to the light supplying/guiding member 30. The light source 20 has, for example, a laser light source for emitting a laser beam or an LED light source for emitting an LED beam.

As shown in FIG. 1A, the light supplying/guiding member 30 has one end portion 31a optically connected to the light source 20 (connector 21), and the other end portion 31b optically connected to a reflection mechanism 70, which will be described later and emitting the light guided from the one end portion 31a to the reflection mechanism 70. The light supplying/guiding member 30 has, for example, flexibility. The light supplying/guiding member 30 has, for example, an optical fiber. The light supplying/guiding member 30 extends, for example, in the lengthwise direction of the optical sensor 10. One light supplying/guiding member 30 is provided.

As shown also in FIG. 1A, the characteristic light-guiding member 40 has one end portion 41a optically connected to a reflection mechanism 70, and being incident the light reflected by the reflection mechanism 70, and the other end portion 41b optically connected to the detecting unit 60 through a connector 61 and configured to guide to the detecting unit 60 the light guided from the one end portion 41a. The characteristic light-guiding member 40 extends, for example, in the lengthwise direction of the optical sensor 10, and is provided parallel to the light supplying/guiding member 30. The characteristic light-guiding member 40 is provided in plurality. The characteristic light-guiding members 40 are provided, surrounding the light supplying/guiding member 30.

The characteristic light-guiding member 40 has, for example, flexibility. The characteristic light-guiding member 40 has, for example, an optical fiber. As shown in FIG. 1B and FIG. 1C, the characteristic light-guiding member 40 has a core 43a, a cladding 43b covering the core 43a, and a jacket 43c covering and protecting the cladding 43b. A one part of the cladding 43b and a one part of the jacket 43c are cut, in a slit, the characteristic changing part 50 is provided. The characteristic changing part 50 is thus embedded in the characteristic light-guiding member 40. The inner circumferential surface of the characteristic changing part 50 contacts the core 43a, the outer circumferential surface of the characteristic changing part 50 does not protrude from the outer circumferential surface of the jacket 43c in a radial direction of the characteristic light-guiding member 40, is flush with the outer circumferential surface of the jacket 43c. Sides of the characteristic changing part 50 contact sides of the cladding 43b and sides of the jacket 43c. The characteristic changing part 50 need not fill up the slit, and may have appropriate hardness and appropriate thickness. In this case, the thickness of the characteristic changing part 50 can be designed in accordance with the response of light of the characteristic changing part 50.

The characteristic changing part 50 may have, for example, a light absorbing part for absorbing light. In this case that the characteristic changing part 50 has the light absorbing part, the light intensity the characteristic changing part 50 absorbs depends on how much the characteristic light-guiding member 40 is bent. For example, when the characteristic light-guiding member 40 is bent upwards so that the characteristic changing part 50 is positioned inside the characteristic light-guiding member 40, the characteristic changing part 50 will absorb less light than in the case where the characteristic light-guiding member 40 extends straight. When the characteristic light-guiding member 40 is bent downwards, so that the characteristic changing part 50 is positioned outside the characteristic light-guiding member 40, the characteristic changing part 50 will absorb more light than in the case where the characteristic light-guiding member 40 extends straight. As the light intensity the characteristic changing part 50 absorbs increases or decreases, the light intensity propagated to the detecting unit 60 changes.

Thus, for example, the characteristic changing part 50 changes the optical characteristic in accordance with, for example, how much the characteristic light-guiding member 40 is bent. The characteristic changing part 50 is provided at a desired point in the lengthwise direction of the characteristic light-guiding member 40.

As shown in FIG. 1B, the characteristic light-guiding member 40 including the characteristic changing part 50 is covered with a protective member 43d and is protected by the protective member 43d. The protective member 43d may cover only the characteristic changing part 50, as shown in FIG. 1C. The protective member 43d can be dispensed with.

The characteristic light-guiding member 40 may be either integral with, or a member independent of, the light supplying/guiding member 30. The characteristic light-guiding member 40 is narrower than the light supplying/guiding member 30, and is provided in plurality.

As shown in FIG. 1A, the reflection mechanism 70 has a transmitting member 71 which is optically connected the other end portion 31b of the light supplying/guiding member 30 and the one end portion 41a of the characteristic light-guiding member 40, and the light emitted from the other end portion 31b of the light supplying/guiding member 30 is transmitted through and a reflecting part 73 which reflects the light so that the light transmitting through the transmitting member 71 is incident to the light to the one end portion 41a of the characteristic light-guiding member 40.

One end of the transmitting member 71 is optically connected to the other end portion 31b and the one end portion 41a, the entire surface of the other end of the transmitting member 71 has the reflecting part 73. The light reflected by the reflecting part 73 again transmits through the transmitting member 71 and is incident to the one end portion 41a of the characteristic light-guiding member 40.

If the characteristic changing part 50 has a light absorbing part, the detecting unit 60 detects how much the characteristic light-guiding member 40 is bent, by detecting the change in light quantity due to the characteristic changing part 50.

As also shown in FIG. 1A, the optical sensor 10 has a control member 80 which is provided along the characteristic light-guiding member 40, inhibits at least the twisting of the characteristic light-guiding member 40, and controls a bending state of the characteristic light-guiding member 40 and a positioning mechanism 90 which holds the characteristic light-guiding member 40 and the control member 80, and positions the characteristic changing part 50 with respect to at least the circumferential direction of the characteristic light-guiding member 40 accompanying holding.

Figure 1E:
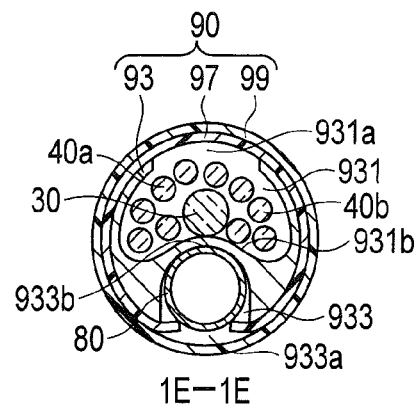
FIG. 1E is a sectional view taken along line 1E-1E shown in FIG. 1A.

As seen from FIG. 1A and FIG. 1E, the control member 80 functions as an axle of the optical sensor 10. Thus, the control member 80 controls the optical sensor 10 including the characteristic light-guiding member 40, setting it to a desired state. Specifically, the control member 80 inhibits the twisting of the bent characteristic light-guiding member 40. The control member 80 is fixed to a support member 93 and a fixing member 95 (both described later), positioning the characteristic light-guiding member 40 with respect to its axial direction and its circumferential direction. The control member 80 has flexibility and may be bent.

The control member 80 is provided, extending, for example, in the lengthwise direction of the optical sensor 10, and is provided parallel to the light supplying/guiding member 30 and the characteristic light-guiding member 40. The control member 80 is provided in the support member 93 and the fixing member 95 (both described later).

The control member 80 is formed by at least one of a hollow cylindrical member as shown in FIG. 1E, and a liner-like member.

The hollow cylindrical member is formed by at least one for example, an elastic member, a resin or metal tube, a helical tube and a helical tube covered with a mesh tube.

The helical tube is shaped like a hollow cylinder made by helically winding a thin metal band made of, for example, stainless steel. The helical tube is, for example, a metal helical tube having a wall thickness. The helical tube is formed of, for example, a spring coil. The mesh tube is formed by weaving a plurality of bundles, such bundle composed of, for example, stainless-steel filaments.

The liner-like member is formed by, for example, bundling a plurality of wires together and then twisting the resultant bundle of wires.

As shown in FIG. 1A, the positioning mechanism 90 has an one end fixing member 91 which an one end portion of the control member 80 fixes, a support member 93 which supports the light supplying/guiding member 30, the one characteristic light-guiding member 40a, the other characteristic light-guiding members 40b, and the control member 80 and a fixing member 95 which the characteristic light-guiding member 40b and the control member 80 fixes to position the characteristic changing part 50.

As shown in FIG. 1D, the one end fixing member 91 is shaped like a round pillar. The one end fixing member 91 has an insertion hole portion 91a, in which one end portion of the control member 80 is inserted. The insertion hole portion 91a extends, for example, in the axial direction of the one end fixing member 91. Once one end portion of the control member 80 is inserted in the insertion hole portion 91a, it is fixed, for example, by adhesion to the one end fixing member 91. The control member 80 is thereby positioned with respect to the axial direction and the circumferential direction of the control member 80.

As shown in FIG. 1D, an outer circumferential surface of the one end fixing member 91 is fixed by, for example, adhesion to an inner circumferential surface of a hollow cylindrical member 99 (described later). As shown in FIG. 1A, one end portion of the outer circumferential surface of the one end fixing member 91 is exposed from the hollow cylindrical member 99 and a exposed part is fixed to the high-precision device. The optical sensor 10 is thereby positioned with respect to its axial direction and its circumferential directions.

As shown in FIG. 1A, the support member 93 is provided in the lengthwise direction of the characteristic light-guiding member 40, for example, between the one end fixing member 91 and the fixing member 95, and between the fixing member 95 and the light source 20. As shown in FIG. 1E, the support member 93 is shaped like a round pillar.

As shown in FIG. 1E, the support member 93 has an insertion hole portion 931 which the light supplying/guiding member 30 and the characteristic light-guiding member 40 are insertable into along the axial direction of the support member 93 and a fixing hole portion 933 which the control member 80 is inserted and fixed, along the axial direction of the support member 93. The insertion hole portion 931 and the fixing hole portion 933 are provided along the axial direction of the support member 93. The insertion hole portion 931 is independent of the fixing hole portion 933.

As shown in FIG. 1E, the insertion hole portion 931 has an insertion/communication part 931a which communicates with the outside so that the light supplying/guiding member 30 and the characteristic light-guiding member 40 are insertable into the insertion hole portion 931 from the outer circumferential surface side of the support member 93. The insertion hole portion 931 and the insertion/communication part 931a are provided in the form of recess portions.

The insertion hole portion 931 has an abutment surface 931b on which the light supplying/guiding member 30 and the characteristic light-guiding member 40 abut when the light supplying/guiding member 30 and the characteristic light-guiding member 40 are inserted into the insertion hole portion 931.

As shown in FIG. 1E, the fixing hole portion 933 has a fixing/communicating part 933a which communicates with the outside so that the control member 80 is insertable into the fixing hole portion 933 from the outer circumferential surface side of the support member 93. The fixing hole portion 933 and the fixing/communicating part 933a are provided in the form of recess portions. When the control member 80 is inserted in the fixing hole portion 933 from the fixing/communicating part 933a, the control member 80 is fixed to the support member 93 by means of, for example, adhesion. The control member 80 is thereby positioned with respect to its axial direction and its circumferential direction. In other words, as shown in FIG. 1A the control member 80 positions the support member 93 with respect to the axial directions of the support member 93 and the circumferential direction of the support member 93. At the same time, the control member 80 is prevented from falling off the support member 93, at the fixing/communicating part 933a.

The fixing hole portion 933 has an abutment surface 933b on which the control member 80 abuts when the control member 80 is inserted into the fixing hole portion 933.

As shown in FIG. 1E, the fixing/communicating part 933a is shifted to the insertion hole portion 931 in the circumferential direction of the support member 93.

As shown in FIG. 1E, the support member 93 holds a desired distance in the diameter direction of the support member 93 between light-guiding member which indicates the light supplying/guiding member 30 and the characteristic light-guiding member 40 and the control member 80.

Figure 1F:
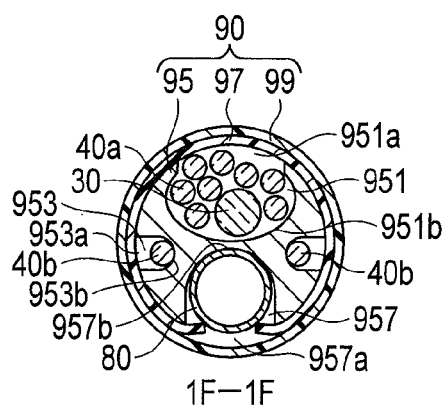
FIG. 1F is a sectional view taken along line 1F-1F shown in FIG. 1A.

As shown in FIG. 1A, the fixing member 95 is provided between, for example, the one support member 93 and the other support member 93, in the lengthwise direction of the characteristic light-guiding member 40. The fixing member 95 is provided to sandwich the characteristic changing part 50 in the lengthwise direction of the characteristic light-guiding member 40. As shown in FIG. 1F, the fixing member 95 is shaped like a round pillar, for example.

As shown in FIG. 1F, the fixing member 95 has an insertion hole portion 951 which the light supplying/guiding member 30 and a one characteristic light-guiding members 40a may be inserted into in the axial direction of the fixing member 95, a characteristic fixing hole portion 953 which the other characteristic light-guiding member 40b is inserted into and is fixed to in the axial direction of the fixing member 95 and a control hole portion 957 which the control member 80 is inserted into and is fixed to in the axial direction of the fixing member 95. The insertion hole portion 951, the characteristic fixing hole portion 953, and the control hole portion 957 extend in, for example, the axial direction of the fixing member 95. The insertion hole portion 951, for example, is larger than the characteristic fixing hole portion 953 and the control hole portion 957, and the control hole portion 957, for example, is larger than the characteristic fixing hole portion 953. The insertion hole portion 951, the characteristic fixing hole portion 953 and the control hole portion 957 are independent of one another.

One of characteristic light-guiding member 40a has characteristic changing parts 50 that need not be positioned, for example, the other characteristic light-guiding member 40b has characteristic changing parts 50 that needs to be positioned, for example. The position indicates a position of the characteristic changing part 50 in the lengthwise direction of the optical sensor 10 for example and also a position of the characteristic changing part 50 in the circumferential direction of the characteristic light-guiding member 40, in other words, orientation of the characteristic changing part 50, while the characteristic light-guiding member 40 remains prevented from being twisted.

As shown in FIG. 1F, the insertion hole portion 951 has a insertion/communication part 951a that communicates with the outside so that the light supplying/guiding member 30 and a part of the characteristic light-guiding member 40 are insertable into the insertion hole portion 951 from the outer circumferential surface side of the fixing member 95. The insertion hole portion 951 and the insertion/communication part 951a are provided in the form of recess portions.

The insertion hole portion 951 has an abutment surface 95b on which the light supplying/guiding member 30 and a part of the characteristic light-guiding member 40a abut when they are inserted into the insertion hole portion 951.

As shown in FIG. 1F, the characteristic fixing hole portion 953 has a characteristic communication part 953a which communicates with the outside so that the other characteristic light-guiding member 40b is insertable into the characteristic fixing hole portion 953 from the outer circumferential surface side of the fixing member 95. The characteristic fixing hole portion 953 and the characteristic communication part 953a are provided in the form of recess portions. When the other characteristic light-guiding member 40b inserted into the characteristic fixing hole portion 953 from the characteristic communication part 953a, the other characteristic light-guiding member 40b is fixed to the fixing member 95 by means of, for example, adhesion. The other characteristic light-guiding member 40b and the characteristic changing part 50 are thereby positioned with respect to the axial direction of the other characteristic light-guiding member 40b and the circumferential direction of the other characteristic light-guiding member 40b. In other words, as shown in FIG. 1A, the other characteristic light-guiding member 40b positions the fixing member 95 in the axial direction of the fixing member 95 and the circumferential direction of the fixing member 95. At the same time, the other characteristic light-guiding member 40b is prevented from failing off the fixing member 95, through the characteristic communication part 953a.

For example, two characteristic fixing hole portions 953 may be provided, symmetrically with respect to the center line of the fixing member 95.

The other characteristic light-guiding member 40b is fixed to one fixing member 95 (i.e., to the left side shown in FIG. 1A), and is not fixed to the other fixing member 95 (i.e., to the right side shown in FIG. 1A). Hence, the characteristic light-guiding member 40b can be freely inserted into the characteristic fixing hole portion 953 provided in the other fixing member 95 along the axis direction the other fixing member 95.

As shown in FIG. 1F, the characteristic fixing hole portion 953 has an abutment surface 953b on which the other characteristic light-guiding member 40b abuts when the other characteristic light-guiding member 40b is inserted into the characteristic fixing hole portion 953.

As shown in FIG. 1F, the control hole portion 957 has a control/communication part 957a that communicates with the outside so that the control member 80 is insertable into the control hole portion 957 from the outer circumferential surface side of the fixing member 95. The control hole portion 957 and the control/communication part 957a are provided in the form of recess portions. When the control member 80 is inserted in the control hole portion 957 from the control/communication part 957a, the control member 80 is fixed to the fixing member 95 by means of, for example, adhesion. The control member 80 is thereby positioned in the axial direction and the circumferential direction of the control member 80. In other words, the control member 80 positions the fixing member 95 in the axial direction and the circumferential direction of the fixing member 95, as shown in FIG. 1A. At the same time, the control member 80 prevents the fixing member 95 from falling off the fixing member 95 through the control/communication part 957a.

The control hole portion 957 has an abutment surface 957b on which the control member 80 abuts when the control member 80 is inserted into the control hole portion 957.

As shown in FIG. 1F, the insertion/communication part 951a, the characteristic fixing hole portion 953, and the control/communication part 957a are shifted to one another in the circumferential direction of the fixing member 95.

As also shown in FIG. 1F, the fixing member 95 holds a desired distance in the diameter direction of the fixing member 95 between light-guiding member which indicates the light supplying/guiding member 30 and one characteristic light-guiding member 40, other characteristic light-guiding member 40b, and the control member 80 by the insertion hole portion 951, the characteristic fixing hole portion 953 and the control hole portion 957.

As shown in FIG. 1A, the fixing member 95 has a specific length, securing the other characteristic light-guiding member 40b and the control member 80 and positioning the characteristic changing part 50 in the axial direction of the characteristic changing part 50.

As shown in FIGS. 1E and 1F, in the support member 93 and the fixing member 95, the insertion hole portion 931 is larger than the insertion hole portion 951 and the insertion hole portion 953. The insertion hole portion 931 is provided overlapping the insertion hole portion 951 and the characteristic fixing hole portion 953 when seen in the lengthwise direction of the characteristic light-guiding member 40. The insertion hole portion 931 and the insertion hole portion 951 are provided in almost the same line one another, in the lengthwise direction of the characteristic light-guiding member 40. The insertion hole portion 931 is provided in almost the same line to the insertion hole portion 951 and the characteristic fixing hole portion 953, in the lengthwise direction of the characteristic light-guiding member 40.

The insertion/communication part 931a has almost the same size as, for example, the insertion/communication part 951a. The insertion/communication part 931a and the insertion/communication part 951a are provided in almost in the same line one another, in the lengthwise direction of the characteristic light-guiding member 40.

Also, the fixing hole portion 933 and the control hole portion 957 are provided almost in the same line one another, in the lengthwise direction of the characteristic light-guiding member 40. The fixing hole portion 933 and the control hole portion 957 have almost the same size one another. The fixing/communicating part 933a and the control/communication part 957a are provided in almost the same line one another, in the lengthwise direction of the characteristic light-guiding member 40.

The positioning mechanism 90 has a cover member 97 which covers the support member 93 and the fixing member 95 as shown in FIGS. 1E and 1F, and a hollow cylindrical member 99 which integrally covers a whole portion including the light supplying/guiding member 30, the characteristic light-guiding member 40, reflection mechanism 70, the control member 80, the one end fixing member 91, the support member 93, the fixing member 95 and the cover member 97.

As shown in FIG. 1E and FIG. 1F, the cover member 97 is shaped like a hollow cylinder, and contacts the support member 93 and the fixing member 95.

As shown in FIG. 1E, the cover member 97 covers the support member 93 including the insertion/communication part 931a, preventing the light supplying/guiding member 30 and the characteristic light-guiding member 40 from falling off from the support member 93 through the insertion/communication part 931a. At the same time, the cover member 97 covers at least one part of the fixing/communicating part 933a as shown in FIG. 1E, preventing the control member 80 from falling off from the support member 93 through the fixing/communicating part 933a. At the same time, the cover member 97 pushes the control member 80 to the abutment surface 933b via the fixing/communicating part 933a so that the control member 80 is fixed to the support member 93.

As shown in FIG. 1F, the cover member 97 covers the fixing member 95 including the insertion/communication part 951a and the characteristic communication part 953a, preventing the light supplying/guiding member 30 and one characteristic light-guiding member 40a from falling off from the fixing member 95 through the insertion/communication part 951a, and preventing the other characteristic light-guiding member 40b from falling off from the fixing member 95 through the characteristic communication part 953a. At the same time, the cover member 97 covers at least one part of control/communication part 957a, as shown in FIG. 1F, preventing the control member 80 from falling off from the fixing member 95 through the control/communication part 957a. At the same time, the cover member 97 pushes the control member 80 to the abutment surface 957b via the control/communication part 957a, as shown in FIG. 1F, so that control member 80 is fixed to the fixing member 95.

As shown in FIG. 1A, in the hollow cylindrical member 99, the light supplying/guiding member 30, the characteristic light-guiding member 40, control member 80, reflection mechanism 70, the one end fixing member 91, support member 93, fixing member 95, and the cover member 97 are inserted in the hollow cylindrical member 99. The hollow cylindrical member 99 has flexibility. As shown in FIG. 1D, FIG. 1E, and FIG. 1F, the hollow cylindrical member 99 is adhered to the one end fixing member 91.

Figure 1G:
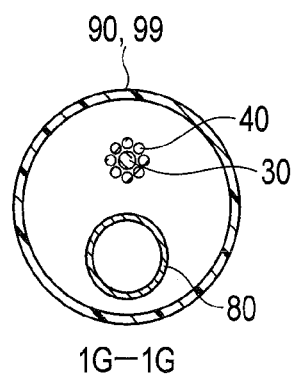
FIG. 1G is a sectional view taken along line 1G-1G shown in FIG. 1A.

As shown in FIGS. 1A, 1G, and 1H, the hollow cylindrical member 99 surrounds the light supplying/guiding member 30, the characteristic light-guiding member 40, and the control member 80, respectively between the one end fixing member 91 and the support member 93, between the support member 93 and the fixing member 95, and between the fixing member 95 and the other fixing member 95.

As shown in FIG. 1G, the light supplying/guiding member 30 and the characteristic light-guiding member 40 are bundled together in the region between the one end fixing member 91 and the support member 93. At this point, the light supplying/guiding member 30 is surrounded by the characteristic light-guiding member 40. The characteristic light-guiding member 40 is composed of, for example, the core 43a only.

As described above, the other characteristic light-guiding member 40b is fixed to the fixing members 95, and is positioned with respect to the axial direction and the circumferential direction of the characteristic light-guiding member 40. As shown in FIG. 1A, the characteristic changing part 50 provided between one fixing member 95 and the other fixing member 95 is therefore positioned with respect to the axial direction and the circumferential direction of the characteristic light-guiding member 40. Thus, in the characteristic changing part 50, a position in the lengthwise direction of the optical sensor 10 and a position of the characteristic changing part 50 in the circumferential direction of the characteristic light-guiding member 40, in other words, orientation of the characteristic changing part 50 is fixed.

[Operation]

The light source 20 emits light. The light is incident to the light supplying/guiding member 30 and guided by the light supplying/guiding member 30 to the reflection mechanism 70. In the reflection mechanism 70, the light transmits through the transmitting member 71, is reflected by the reflecting part 73, transmits through the transmitting member 71 again, and is incident to the characteristic light-guiding member 40. Then the light is guided by the characteristic light-guiding member 40 to the detecting unit 60. At this point, the optical characteristic of the light changes by the characteristic changing part 50 in accordance with how much the characteristic light-guiding member 40 is bent. The light with changed optical characteristic is incident to the detecting unit 60 through the connector 21, and is detected by the detecting unit 60.

As shown in FIG. 1A, the control member 80 is thicker than the light supplying/guiding member 30 and the characteristic light-guiding member 40, and extends along the characteristic light-guiding member 40. As shown in FIG. 1E and FIG. 1F, the control member 80 inhibits the twisting of the characteristic light-guiding member 40 bent by being fixed to the support member 93 and the fixing member 95. As shown in FIG. 1F, the characteristic light-guiding member 40 is fixed to the fixing member 95, and is positioned with respect to the axial direction and the circumferential direction of the characteristic light-guiding member 40.

Thus, when the optical sensor 10 is incorporated into the high-precision device, the twisting and dislocation of the characteristic light-guiding member 40 are prevented, the characteristic changing part 50 can be reliably positioned. Therefore, the detecting unit 60 reliably detects how much the characteristic light-guiding member 40 is bent.

As shown in FIG. 1E, the support member 93 keeps at a desired distance between the characteristic light-guiding member 40 and the control member 80, as shown in FIG. 1F, the fixing member 95 is fixed to the characteristic light-guiding member 40 and the control member 80. The characteristic changing part 50 is thereby reliably positioned with respect to the axial direction, the circumferential direction, and the diameter direction of the characteristic light-guiding member 40b.

The characteristic light-guiding member 40 is fixed to one fixing member 95 only. The control member 80 has flexibility to bending. Therefore, the characteristic light-guiding member 40 can bend without being influenced by the control member 80.

When the optical sensor 10 is assembled, the control member 80 is provided at the support member 93 (fixing hole portion 933) through the fixing/communicating part 933a as shown in FIG. 1E, and is provided at the fixing member 95 (control hole portion 957) through the control/communication part 957a as shown in FIG. 1F. Since the fixing/communicating part 933a and the control/communication part 957a are provided in the same line one another, the control member 80 can easily be provided at the support member 93 and the fixing member 95.

The light supplying/guiding member 30 and the characteristic light-guiding member 40a are provided in the support member 93 (insertion hole portion 931) through the insertion/communication part 931a as shown in FIG. 1E, and are provided in the fixing member 95 (insertion hole portion 951) through the insertion/communication part 951a as shown in FIG. 1F. Since the insertion/communication part 931a and the insertion/communication part 951a are provided in the same line one another, the light supplying/guiding member 30 and the characteristic light-guiding member 40a can be easily provided at the support member 93 and the fixing member 95.

The characteristic light-guiding member 40b is provided in the support member 93 (insertion hole portion 931) through the insertion/communication part 931a as shown in FIG. 1E, and are provided in the fixing member 95 (characteristic fixing hole portion 953) through the characteristic communication part 953a as shown in FIG. 1F.

At this point, the cover member 97 covers the insertion/communication part 931a and the fixing/communicating part 933a at the support member 93 as shown in FIG. 1E, preventing the light supplying/guiding member 30, the characteristic light-guiding member 40 and the control member 80 from falling off from the support member 93.

At the fixing member 95 shown in FIG. 1F, the cover member 97 covers the insertion/communication part 951a, the characteristic communication part 953a, and the control/communication part 957a, preventing the light supplying/guiding member 30, one characteristic light-guiding member 40a, the other characteristic light-guiding member 40b, and the control member 80 from falling off from the fixing member 95.

The cover member 97 pushes the control member 80 to the abutment surface 933b of the fixing hole portion 933 as shown in FIG. 1E, and pushes the control member 80 to the abutment surface 957b of the control hole portion 957 as shown in FIG. 1F.

The characteristic changing part 50 is thereby reliably positioned.

As shown in FIG. 1A, the hollow cylindrical member 99 covers the whole portion including the light supplying/guiding member 30, the characteristic light-guiding member 40, the reflection mechanism 70, the control member 80, the one end fixing member 91, support member 93, fixing member 95, and cover member 97. These components can therefore be protected from external forces, and be protected from impacts, etc.

[Advantages]

In the embodiment described above, the control member 80 inhibits the twisting of the bent characteristic light-guiding member 40, and the positioning mechanism 90 positions the characteristic light-guiding member 40 with respect to the axial direction and the circumferential direction of the characteristic light-guiding member 40. Therefore, the characteristic changing part 50 can be reliably positioned, and the detecting units 60 can easily and accurately detect how much the characteristic light-guiding member 40 is bent.

In this embodiment, the desired distance between the characteristic light-guiding member 40 and the control member 80 is maintained by the support member 93, and the characteristic light-guiding member 40 and the control member 80 are fixed to the fixing member 95. The characteristic changing part 50 can therefore be positioned with respect to the axial direction, the circumferential direction and the diameter direction of the characteristic light-guiding member 40*b*.

Also, in this embodiment, the control member 80 may be an elastic member including, for example, a densely wound coil, then, the optical sensor 10 can have a small diameter.

In this embodiment, the control member 80 may be a helical tube, in this case, the control member 80 can more readily inhibit the twisting of the bent characteristic light-guiding member 40.

Furthermore, in this embodiment, the control member 80 may be a stranded wire member, in this is the case, the optical sensor 10 can have a small diameter.

In this embodiment, when the optical sensor 10 is assembled, the control member 80 is provided into the support member 93 (fixing hole portion 933) through the fixing/communicating part 933*a* as shown in FIG. 1E, and is provided into the fixing member 95 (control hole portion 957) through the control/communication part 957*a* as shown in FIG. 1F. This saves time and labor of inserting through the control member 80 into the support member 93 and the fixing member 95. Since the fixing/communicating part 933*a* and the control/communication part 957*a* are arranged in the same line one another, the control member 80 can be easily and simultaneously provided at the support member 93 and the fixing member 95. Thus, the optical sensor 10 according to this embodiment can be assembled with ease.

Also in this embodiment, when the optical sensor 10 is assembled, the light supplying/guiding member 30 and the characteristic light-guiding member 40*a* are provided into the support member 93 (insertion hole portion 931) through the insertion/communication part 931*a*, as shown in FIG. 1E, and are provided into the fixing member 95 (insertion hole portion 951) through the insertion/communication part 951*a*, as shown in FIG. 1F. This saves time and labor of inserting through the light supplying/guiding member 30 and the characteristic light-guiding member 40*a* into the support member 93 and the fixing member 95, respectively. Since the insertion/communication part 931*a* and the insertion/communication part 951*a* are provided in the same line one another, the light supplying/guiding member 30 and the characteristic light-guiding member 40*a* can be easily and simultaneously provided at the support member 93 and the fixing member 95, respectively. The optical sensor 10 according to this embodiment can therefore be easily assembled.

In this embodiment, when the optical sensor 10 is assembled, the characteristic light-guiding member 40*b* is provided into the support member 93 (insertion hole portion 931) through the insertion/communication part 931*a*, as shown in FIG. 1E, and is provided into the fixing member 95 (characteristic fixing hole portion 953), as shown in FIG. 1F. This saves time and labor of inserting through the characteristic light-guiding member 40 into the support member 93 and the fixing member 95 in this embodiment.

Also in this embodiment, the cover member 97 covers the insertion/communication part 931*a* and the fixing/communicating part 933*a* in the support member 93, as shown in FIG. 1E. The cover member 97 therefore prevents the light supplying/guiding member 30, the characteristic light-guiding member 40, and the control member 80 from falling off from the support member 93.

In this embodiment, the cover member 97 covers the insertion/communication part 951*a*, and characteristic communication part 953*a*, and the control/communication part 957*a* in the fixing member 95, as shown in FIG. 1F. The cover member 97 can therefore prevent the light supplying/guiding member 30, one the characteristic light-guiding member 40*a*, the other characteristic light-guiding member 40*b*, and the control member 80 from falling off from the fixing member 95.

In this embodiment, the cover member 97 pushes the control member 80 to the abutment surface 933*b* of the fixing hole portion 933 as shown in FIG. 1E, and pushes the control member 80 to the abutment surface 957*b* of the control hole portion 957 as shown in FIG. 1F.

Thus, in this embodiment, the control member 80 can be fixed to the support member 93 and the fixing member 95, the characteristic changing parts 50 can therefore be reliably positioned.

In this embodiment, when the light supplying/guiding member 30, the characteristic light-guiding member 40, and the control member 80 are abutted on the abutment surfaces 931*b*, 933*b*, 951*a*, 953*b*, and 957*b*, the light supplying/guiding member 30, the characteristic light-guiding member 40, and the control member 80 can therefore be easily positioned to the support member 93 and the fixing member 95.

Also in this embodiment, as shown in FIG. 1A, the hollow cylindrical member 99 covers the whole portion including the light supplying/guiding member 30, the characteristic light-guiding member 40, the reflection mechanism 70, the control member 80, the one end fixing member 91, the support member 93, fixing member 95, and the cover member 97. These components can therefore be protected from external forces, and be protected from impacts, etc.

In this embodiment, the reflection mechanism 70 need not be provided if the optical sensor 10 is provided so that the light emitted from the light source 20 is turned back at the one end portion 41*a* (i.e., relay point) of the characteristic light-guiding member 40 and then propagates to the detecting units 60.

The characteristic changing parts 50 may have a wavelength changing member (e.g., phosphor) that changes the wavelength of the light. If the characteristic changing parts 50 has the wavelength changing member, the light intensity changed in wavelength by the characteristic changing part 50 differs in accordance with how much the characteristic light-guiding member 40 is bent. If the characteristic light-guiding member 40 is bent upwards so that the characteristic changing part 50 is positioned inside the characteristic light-guiding member 40, the light intensity changed in wavelength by the characteristic changing part 50 will decrease more than in the case the characteristic light-guiding member 40 extends straight. If the characteristic light-guiding member 40 is bent downwards so that the characteristic changing part 50 is positioned outside the characteristic light-guiding member 40, the light intensity changed in wavelength by the characteristic changing part 50 will increase more than in the case the characteristic light-guiding member 40 extends straight. Thus, the light intensity propagating to the detecting unit 60 changes when the light intensity changed in wavelength by the characteristic changing part 50 changes.

In this embodiment, the characteristic changing part 50 changes the optical characteristic in accordance with, for example, the bending amount of the characteristic light-guiding member 40, however it is not necessarily limited to this. The characteristic changing part 50 may change the optical characteristic in accordance with, for example, at least one of the bending direction of the characteristic light-guiding member 40, the bending amount of a high-precision device, the bending direction of the high-precision device, or how much the high-precision device is manipulated.

The cover member 97 independently covers at least of the support member 93 and the fixing member 95.

[First Modification]

As shown in FIG. 2, the insertion/communication part 931*a* and the insertion/communication part 951*a* are shifted in the circumferential direction of the characteristic light-guiding member 40 in this modification. Therefore, an edge 931*c* of the insertion hole portion 931 and an edge 951*c* of the insertion hole portion 951 are shifted, thus the light supplying/guiding member 30 and the characteristic light-guiding member 40*a* are prevented from falling off from the support member 93 and the fixing member 95.

The insertion/communication part 931*a* in the support member 93 and the insertion/communication part 951*a* in the fixing members 95 have been described, however they are not necessarily limited to this. The insertion/communication parts 931*a* in the support member 93*s* are similar to the insertion/communication parts 931*a* in other support members 93. The same holds true of the fixing members 95.

In the modification, the insertion/communication parts 931*a*, the insertion/communication part 931*a* and the insertion/communication part 951*a*, the insertion/communication parts 951*a*, the insertion/communication part 931*a* and the characteristic communication part 953*a*, the characteristic communication parts 953*a*, the fixing/communicating parts 933*a*, the fixing/communicating part 933*a* and the control/communication part 957*a*, and the control/communication parts 957*a* may be provided along the same line in the axis direction of the characteristic light-guiding member 40, or may be shifted in the circumferential direction of the characteristic light-guiding member 40.

[Second Modification]

As shown in FIG. 3, the light supplying/guiding member 30 is pushed by a control member 80 made of, for example, a spring coil, and may thereby be fixed to the fixing member 95. Therefore, the cover member 97 can be eliminated, and the optical sensor 10 can be made thinner. The fixing member 95 is used in explaining the modification of this embodiment, but is not necessarily limited to this, and may be similarly applied to support member 93.

[Third Modification]

The shape of the support member 93 is not limited to the shape specified above. As shown in FIG. 4A, the support member 93 may have a U-shaped insertion hole portion 931, a fixing hole portion 933 surrounded by a insertion hole portion 931, and a fixing hole portion 935 providing for the other characteristic light-guiding member 40*b*. The fixing hole portion 933 is made in the center of the support member 93.

Moreover, as shown in FIG. 4B, one insertion hole portion 931 and the other insertion hole portion 931 may be provided, symmetric to each other in an up-down direction with respect to the fixing hole portion 933, and one fixing hole portion 935 and the other the fixing hole portion 935 may be provided, symmetric to each other in a left-right direction with respect to the fixing hole portion 933.

As shown in FIG. 4C, the insertion hole portion 931 may be provided, extending along the fixing hole portion 933. The fixing hole portion 933 is surrounded by the insertion hole portion 931 and the fixing hole portion 935.

As shown in FIG. 4D, the insertion hole portion 931 may have an L-shaped cross section so that surrounding the fixing hole portion 933. One fixing hole portion 935 and the other fixing hole portion 935 are spaced 90° apart.

The fixing member 95 is configured in the same way as the support member 93 described above.

Second Embodiment

Figure 5A:
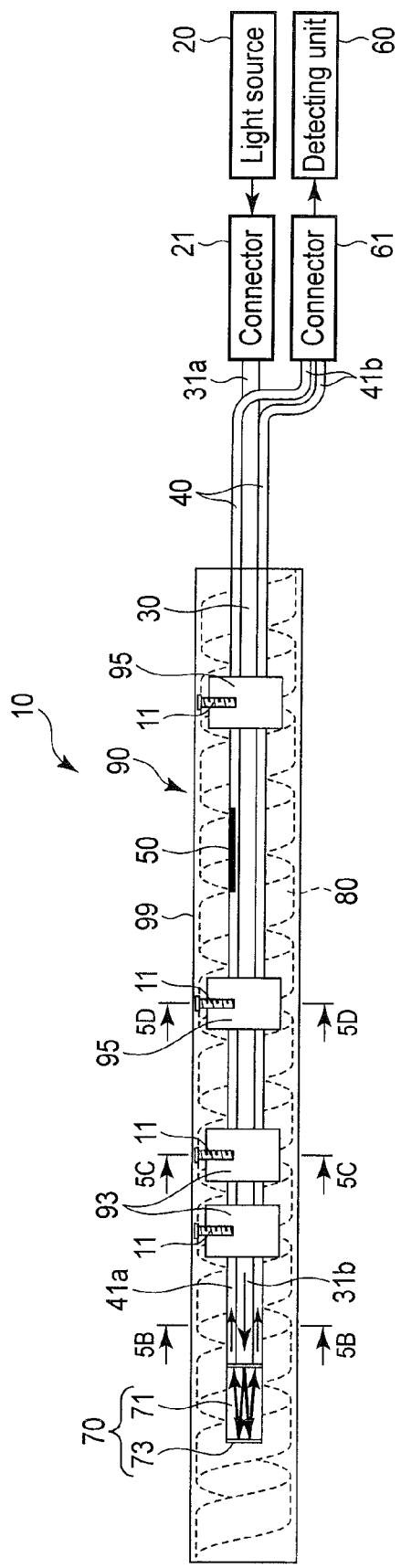
FIG. 5A is a schematic diagram showing an optical system according to a second embodiment.
Figure 5B:
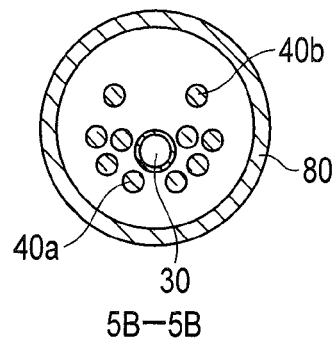
FIG. 5B is a sectional view taken along line 5B-5B shown in FIG. 5A.

As shown in FIG. 5A, the control member 80 is shaped like a hollow cylinder so that surrounding the characteristic light-guiding member 40, the reflection mechanism 70, the support member 93, and the fixing member 95 which are inserted in the control member 80. That is, the control member 80 is provided outside the support member 93 and the fixing member 95. The control member 80 is inserted in a hollow cylindrical member 99.

As shown in FIG. 5A, for example, the control member 80 is formed by a helical tube. The helical tube is, for example, a spring coil. The helical tube may be covered with a mesh tube, or may be composed of helical coils, one wrapped around another.

Figure 5C:
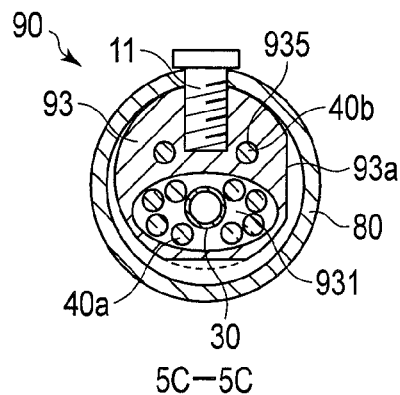
FIG. 5C is a sectional view taken along line 5C-5C shown in FIG. 5A.
Figure 5D:
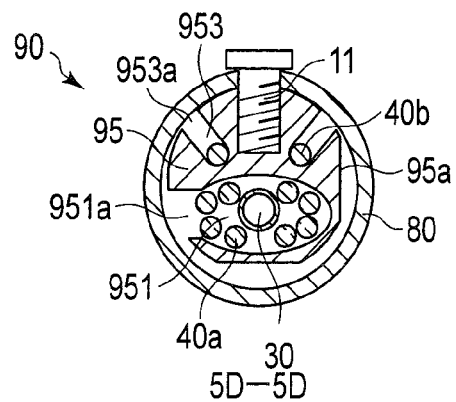
FIG. 5D is a sectional view taken along line 5D-5D shown in FIG. 5A.

As shown in FIG. 5C and FIG. 5D, the control member 80 is fixed to the support member 93 and the fixing member 95 with a fastening member 11 such a screw, or with adhesive.

As shown in FIG. 5C, the support member 93 inserted in the control member 80 has an abutment surface 93*a* which is flat, is provided on a part of the outer circumferential surface of the support member 93, and is formed for facing the characteristic changing part 50. That is, the part of the outer circumferential surface is cut.

As shown in FIG. 5D, the fixing member 95 inserted in the control member 80 has an abutment surface 95*a* which is flat, is provided on a part of the outer circumferential surface of the fixing member 95, and is formed for facing the characteristic changing part 50. That is, the part of the outer circumferential surface is cut.

[Advantages]

In this embodiment, the control member 80 protects the light supplying/guiding member 30 and the characteristic light-guiding member 40, moreover, the characteristic changing part 50 is firmly positioned, enhancing the detection accuracy of the detecting unit 60.

In this embodiment, when the support member 93 and the fixing member 95 is fixed to the control member 80 by the fastening member 11, the abutment surfaces 93*a* and 95*a* increase the area at which the support member 93 and the fixing member 95 contact the control member 80, the support member 93 and the fixing member 95 is easily positioned in the circumferential direction. In this embodiment, therefor, the characteristic changing part 50 is firmly positioned, the contact area is increased, the optical sensor 10 can be more easily assembled.

Third Embodiment

As shown in FIG. 6A, FIG. 6B, and FIG. 6C, the control member 80 serves the light supplying/guiding member 30. Therefore, the control member 80 is formed at least one of the hollow cylindrical member, the liner-like member, and the optical fiber.

The one end fixing member 91 can be therefore eliminated with in this embodiment, and the number of components can be reduced, whereby the optical sensor 10 can be thinner. Otherwise, the characteristic light-guiding members 40 can be increased, the characteristic changing parts 50 can be increased, and the detection accuracy is increased.

As shown in FIG. 6B, the characteristic light-guiding member 40a is independently provided in the insertion hole portion 931 in the support member 93, as shown in FIG. 6B, the characteristic light-guiding member 40b is independently provided in the fixing hole portion 935 of the support member 93.

As shown in FIG. 6C, two characteristic light-guiding members 40a may be provided in the insertion hole portions 951 in the fixing member 95, and two characteristic light-guiding members 40b may be provided in the characteristic fixing hole portions 953 in the fixing member 95.

The characteristic light-guiding members 40b can therefore be positioned more accurately in this embodiment. In this embodiment, the characteristic light-guiding members 40b can be protected from the interference of the characteristic light-guiding members 40a.

The one characteristic light-guiding members 40b may be provided in the same insertion hole portion 931 as shown in FIG. 6D.

The present invention is not limited to the embodiments described above, and the components of any embodiment may be modified in various ways in implementing the invention without deviating from the scope of the invention. Furthermore, the components of any embodiment described above may be combined in various ways as necessary to make different inventions.

What is claimed is:

1. An optical sensor comprising:
   a light source configured to emit light;
   a characteristic light-guiding member configured to guide the light emitted from the light source;
   a characteristic changing part which is provided in the characteristic light-guiding member and configured to change the optical characteristic of the light in accordance with how much the characteristic light-guiding member is bent;
   a detecting unit configured to detect the light having the optical characteristic changed by the characteristic changing part and guided by the characteristic light-guiding member;
   a control member which provided along the characteristic light-guiding member, configured to inhibit at least the twisting of the characteristic light-guiding member, and controls a bending state of the characteristic light-guiding member; and
   a positioning mechanism which holds the characteristic light-guiding member and the control member and positions the characteristic changing part with respect to at least a circumferential direction of the characteristic light-guiding member accompanying holding.

2. The optical sensor according to claim 1, wherein the positioning mechanism includes
   a support member which supports the characteristic light-guiding member and the control member for holding a desired distance between the characteristic light-guiding member and the control member, and
   a fixing member which the characteristic light-guiding member and the control member are fixed to position the characteristic changing part.

3. The optical sensor according to claim 2, wherein the control member is formed at least one of a hollow cylindrical member, a liner-like member and an optical fiber.

4. The optical sensor according to claim 3, wherein the support member includes
   an insertion hole portion which the characteristic light-guiding member are insertable into along an axial direction of the support member, and
   a fixing hole portion which the control member is inserted into along an axial direction of the support member and in which the control member is fixed;
   the insertion hole portion has an insertion/communication part which communicates with the outside so that the characteristic light-guiding member is insertable into the insertion hole portion from the outer circumferential surface side of the support member;
   the fixing hole portion has a fixing/communicating part which communicates with the outside so that the control member is insertable into the fixing hole portion from the outer circumferential surface side of the support member;
   the fixing member includes
   a characteristic fixing hole portion which the characteristic light-guiding member is inserted into and fixed to in the axial direction of the fixing member, and
   a control hole portion which the control member is inserted into and is fixed to in the axial direction of the fixing member;
   the characteristic fixing hole portion has a characteristic communication part which communicates with the outside so that the characteristic light-guiding member is insertable into the characteristic fixing hole portion from the outer circumferential surface side of the fixing member; and
   the control hole portion has a control/communication part which communicates with the outside so that the control member is insertable into the control hole portion from the outer circumferential surface side of the fixing member.

5. The optical sensor according to claim 4, wherein the support member and the fixing member are provided in plurality,
   the insertion/communication parts, the insertion/communication part and the characteristic communication part, the characteristic communication parts, the fixing/communicating parts, the fixing/communicating part and control/communication part, and the control/communication parts are provided along the same line in a lengthwise direction of the characteristic light-guiding member, or are shifted in a circumferential direction of the characteristic light-guiding member.

6. The optical sensor according to claim 4, wherein the positioning mechanism further has a cover member which independently covers at least one of the support member including the insertion/communication part, to prevent the characteristic light-guiding member from falling off from the support member through the insertion/communication part and the fixing member including the characteristic communication part, to prevent the characteristic light-guiding member from falling off from the fixing member through the characteristic communication part;
   the cover member covering the support member covers at least one part of the fixing communication member in order to prevent the control member from falling off from the support member through the fixing communication member; and
   the cover member covering the fixing member covers at least one part of the control/communication part in order to prevent the control member from falling off from the fixing member through the control/communication part.

7. The optical sensor according to claim 4, wherein the positioning mechanism further has a hollow cylindrical member which integrally covers the characteristic light-guiding member, the characteristic changing part, the support member and the fixing member.

* * * * *